(12) United States Patent
Hu

(10) Patent No.: US 11,058,828 B2
(45) Date of Patent: Jul. 13, 2021

(54) SAFE PEN NEEDLE

(71) Applicant: Promisemed Hangzhou Meditech Co., Ltd., Hangzhou (CN)

(72) Inventor: Chaoyu Hu, Hangzhou (CN)

(73) Assignee: PROMISEMED HANGZHOU MEDITECH CO., LTD., Zhejiang Province (CN)

( * ) Notice: Subject to any disclaimer, the term of this patent is extended or adjusted under 35 U.S.C. 154(b) by 0 days.

(21) Appl. No.: 16/616,920

(22) PCT Filed: Dec. 7, 2018

(86) PCT No.: PCT/CN2018/119795
§ 371 (c)(1),
(2) Date: Nov. 25, 2019

(87) PCT Pub. No.: WO2019/218650
PCT Pub. Date: Nov. 21, 2019

(65) Prior Publication Data
US 2020/0360624 A1   Nov. 19, 2020

(30) Foreign Application Priority Data
May 16, 2018   (CN) .......................... 201810467433.6

(51) Int. Cl.
*A61M 5/315* (2006.01)
*A61M 5/32* (2006.01)
*A61K 38/28* (2006.01)

(52) U.S. Cl.
CPC ........ *A61M 5/3257* (2013.01); *A61M 5/3271* (2013.01); *A61M 5/3293* (2013.01); *A61K 38/28* (2013.01); *A61M 2005/3254* (2013.01)

(58) Field of Classification Search
CPC .............. A61M 5/3271; A61M 5/3257; A61M 5/3293; A61M 2005/3254; A61K 38/28
See application file for complete search history.

(56) References Cited

U.S. PATENT DOCUMENTS

| 9,907,916 B2 * | 3/2018 | Evans ................. A61M 5/3272 |
| 2006/0189933 A1 * | 8/2006 | Alheidt ................. A61M 5/326 |
| | | 604/110 |

(Continued)

FOREIGN PATENT DOCUMENTS

| CN | 103079610 A | 5/2013 |
| CN | 104491955 A | 4/2015 |

(Continued)

*Primary Examiner* — Nathan R Price
*Assistant Examiner* — John A Doubrava
(74) *Attorney, Agent, or Firm* — Muncy, Geissler, Olds & Lowe, P.C.

(57) ABSTRACT

A safe insulin pen needle has a structure effectively circumvents the risk of the needle head protection failure caused by the rotation of the insulin pen during the needle pulling process by some users through a first check flange on one side of a first initial fixing position matched with a first elastic clamping jaw. The safe insulin pen needle effectively circumvents the safety risk that the needle tail tends to damage the user through the needle tail protection structure and, at the same time, effectively circumvents the risk that the needle tail protector will rotate and thus the needle tail protection will fail during the separation of the insulin pen from the insulin pen needle through a second check flange on one side of a second initial fixing position matched with a second elastic clamping jaw.

20 Claims, 4 Drawing Sheets

(56) References Cited

U.S. PATENT DOCUMENTS

| | | | | |
|---|---|---|---|---|
| 2008/0177237 A1* | 7/2008 | Stonehouse | ............ | A61M 5/326 604/263 |
| 2009/0024093 A1 | 1/2009 | Carrel et al. | | |
| 2012/0150125 A1* | 6/2012 | Karlsson | ............... | A61M 5/326 604/198 |
| 2014/0107577 A1* | 4/2014 | Boyd | .................. | A61M 5/3213 604/111 |

FOREIGN PATENT DOCUMENTS

| CN | 104771815 A | 7/2015 |
|---|---|---|
| CN | 108543169 A | 9/2018 |
| WO | WO 2014/136652 A1 | 9/2014 |
| WO | WO 2016/066014 A1 | 5/2016 |

\* cited by examiner

SAFE PEN NEEDLE

TECHNICAL FIELD

The invention relates to the technical field of a medical device, in particular to a safe insulin pen needle for injecting insulin.

BACKGROUND ART

The insulin pen needle is a conventional insulin injection device for injecting insulin for treating diabetes. There are many types of insulin injection devices in the prior art, and the advantages and disadvantages of each type of insulin pen needles are also different.

One safe insulin pen needle is disclosed in the Chinese Invention Patent No. CN104491955A and the International Publication No. WO2016/066014A1. The advantage of this type of insulin pen needle is that the protector is triggered during the injection of insulin, after the injection is completed, the tip of the needle is instantly protected to prevent the needle tip from injuring the doctor or patient.

However, there are some drawbacks to the above-mentioned type of safe insulin pen needle, as follows:

In the Chinese Invention Patent No. CN104491955A, a clamping column 13 of a needle hub is initially located at an initial fixing portion 212 of the trigger protector 2. During the injection of the insulin, the clamping column 13 enters the upper end of a transition section 213 along the first guide section 211. After the injection is completed and a needle head is pulled out from the patient's skin, the clamping column enters a second guide section 214 along the transition section under the action of a spring to achieve automatic protection of the needle head by the trigger protector.

When the user correctly uses the above-mentioned insulin pen needle according to the regulations, the above-mentioned trigger protector is effective for automatic protection of the needle head. However, some users have the habit of rotating the insulin pen needle when the needle is pulled out after the insulin injection is completed. During this process, due to the rotation, the clamping column 13 is very likely to enter the first guide section 211 from the transition section, thereby returning to the initial fixing portion 212, the automatic protection of the needle head by the trigger protector fails.

Although the above-mentioned situation in which the automatic protection of the needle head fails due to the rotation of the insulin pen needle during needle removal is a small probability event, it is necessary to improve the above-mentioned insulin pen needle to prevent such a small probability risk event from occurring.

(2) The above-mentioned insulin pen needle only has a trigger protector at the needle head end, and the needle tail end is still in a bare state, and there is still a risk of damage to the user by the needle tail end. Therefore, it is necessary to improve the above-mentioned insulin pen needle to prevent damage to the user from the needle tail end.

SUMMARY OF THE INVENTION

There are two technical problems to be solved by the present invention. One is how to solve the technical defect that the automatic protection of the needle head by the trigger protector fails due to the rotation by users during needle removal after completing the injection of the insulin; and the second is how to solve the technical defect of the damage to the user from the needle tail end.

In order to solve the above technical problem, the technical solution provided by the present invention is as follows:

A safe insulin pen needle, includes at least:

a needle hub, a needle tube being mounted in the needle hub and the needle tube includes at least a needle head and a needle tail;

a needle head protector, sleeving a needle head side of the needle hub, and a first axially compressed spring being disposed between the needle hub and the needle head protector, a first clamping column and a first guide groove which are mutually matched being disposed between the needle hub and the needle head protector, and the first guide groove including at least a first initial fixing section and a first axially extending trigger guide section;

a hub sheath, sleeving the side of the needle hub away from the needle head, and the hub sheath is provided with at least one first elastic clamping jaw in contact with an outer wall of the needle head protector;

where the outer wall of the needle head protector is provided with a first initial fixing position matched with the first elastic clamping jaw, and one side of the first initial fixing position is provided with a first check flange for preventing the first clamping column from entering the first initial fixing section when the first clamping column is located in the first trigger guide section.

For the safe insulin pen needle having the above structure, when the insulin is injected, the needle head protector is triggered, and the clamping column enters the first trigger guide section from the first initial fixing section; during the process of pulling the needle after the insulin injection is completed, under the action of the elastic force of the first spring, the needle head protector moves axially relative to the needle hub. The guiding is achieved by the cooperation between the first clamping column and the first trigger guide section, since the first check flange is provided on one side of the initial fixing position, when a few users with the habit of rotating the insulin pen during pulling the needle rotate the insulin pen, the first check flange prevents the first elastic clamping jaw from entering the first initial fixing position again. That is, the first clamping column can only move along the first trigger guide section and cannot enter the first initial fixing section again.

The safe insulin pen needle having the above structure effectively circumvents the risk of the automatic protection failure of the trigger protector on the needle head due to the rotation during pulling the needle after the injection of the insulin by some users through simple structure settings, so that the automatic protection of needle head protector on the needle head is safer and more reliable.

In a preferred embodiment, the clamping column is disposed on an outer wall of the needle hub, and the first guide groove is disposed on the needle head protector.

In a preferred embodiment, at least two sets of first clamping columns and first guide grooves which are mutually matched and disposed uniformly in a circumferential direction are included. In this embodiment, when two or more pairs of first clamping columns and first guide grooves which are mutually matched are uniformly disposed in the circumferential direction, the axial movement of the needle head protector relative to the needle hub is more stable.

In a preferred embodiment, the first clamping column is disposed on the cantilever structure. In the embodiment of this structure, disposing the first clamping column on the cantilever structure facilitates the completion of the assembly between the needle head protector and the needle hub by using the deformation of the cantilever structure.

In a preferred embodiment, a pair of oppositely disposed protruded jaws is disposed on the side of the first elastic clamping jaw matched with the first initial fixing position, and a partition section adapted to the first check flange is disposed between the pair of protruded jaws. In the structure of this embodiment, a pair of protruded jaws rides over the first check flange in an initial state.

In a preferred embodiment, the needle tail end of the needle hub is internally provided with a needle tail protection structure, the needle tail protection structure includes a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove includes at least a second initial fixing section and a second axially extending trigger guide section. In the structure of this embodiment, the needle tail protector is triggered during the screw-in connection of the insulin pen and the insulin pen needle, and the second spring is in a state of compression and energy storage, during the separation of the insulin pen from the insulin pen needle after the insulin injection is completed, the needle tail protector moves axially relative to the needle hub and completely covers the needle tail under the action of the spring force of the second spring and the guiding action of the second clamping column and the second trigger guide section. The technical problem that the needle tail portion may damage the user is effectively solved by disposing a needle tail protector with the same trigger mechanism as the needle head protector at the needle tail.

In a preferred embodiment, at least two sets of second clamping columns and second guide grooves which are mutually matched and disposed uniformly in a circumferential direction are included, the second clamping column is disposed on an outer wall of the needle tail protector, and the second guide groove is disposed on the protective sleeve.

A safe insulin pen needle includes at least a needle hub, a needle tube is mounted in the needle hub, the needle tube includes at least a needle head and a needle tail, a needle tail protection structure is disposed inside the needle tail end of the needle hub, the needle tail protection structure includes a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove includes at least a second initial fixing section and an axially extending second trigger guide section; the protective sleeve is further provided with a second elastic clamping jaw in contact with the outer wall of the needle tail protector, the outer wall of the needle protector is provided with a second initial fixing position matched with the second elastic clamping jaw, and one side of the second initial fixing position is provided with a second check flange for preventing the second clamping column from entering the second initial fixing section when the second clamping column is located in the second trigger guide section.

The safe insulin pen needle having the above structure has the following technical advantages:

During the screw-in connection of the insulin pen and the insulin pen needle, the needle tail protector is triggered, and the second spring is in a state of compression and energy storage, during the separation of the insulin pen from the insulin pen needle after the insulin injection is completed, the needle tail protector moves axially relative to the needle hub and completely covers the needle tail under the action of the spring force of the second spring and the guiding action of the second clamping column and the second trigger guide section. The technical problem that the needle tail portion may damage the user is effectively solved by disposing the needle tail protector at the needle tail.

In the process of rotating and separating the insulin pen from the insulin pen needle, due to the elastic force of the second spring, the free end face of the needle tail protector is always in contact with the end face of the insulin pen, when the insulin pen is rotated, it is highly probable that the needle tail protector is rotated at the same time under the action of the friction force, so that the risk of the needle tail protection failure is caused by the entrance of the second clamping column into the second initial fixing section again from the second trigger guide section. By disposing the second check flange on the side of the second initial fixing position matched with the second elastic clamping jaw, the second elastic clamping jaw can be effectively prevented from entering into the second initial fixing position due to rotation, i.e., the second clamping column is prevented from entering the second initial fixing section again from the second by trigger guide section, thereby completely solving the technical problem of the above-mentioned needle tail protection failure, and the technical advantages of simple structure and reliable needle tail protection are achieved.

In a preferred embodiment, the second clamping column is disposed on an outer wall of the needle tail protector, and the second guide groove is disposed on the protective sleeve.

In a preferred embodiment, at least two sets of second clamping columns and second guide grooves which are mutually matched and disposed uniformly are included in a circumferential direction.

10—needle hub, 11—needle tube, 111—needle head, 112—needle tail, 12—first spring, 13—first clamping column, 14—cantilever structure, 15—needle tail protection chamber, 20—needle head protector, 21—first guide groove, 211—first initial fixing section, 212—first trigger guide section, 22—first initial fixing position, 23—first check flange, 24—guide inclined surface, 25—first guide surface, 30—hub sheath, 31—first elastic clamping jaw, 32—protruded jaw, 33—partition section, 40—protective sleeve, 41—second elastic clamping jaw, 42—second guide groove, 421—second initial fixing section, 422—second trigger guide section, 50—needle tail protector, 51—second initial fixing position, 52—second check flange, 53—second guide surface, 54—second clamping column, 60—second spring.

DETAILED DESCRIPTION OF THE INVENTION

The present invention will be further described in detail below with reference to the accompanying drawings and embodiments so that the objects, technical solutions, and advantages of the present invention will become more apparent. It is understood that the specific embodiments described herein are merely illustrative of the present invention and are not intended to limit the present invention.

Embodiment 1

Figure 1:
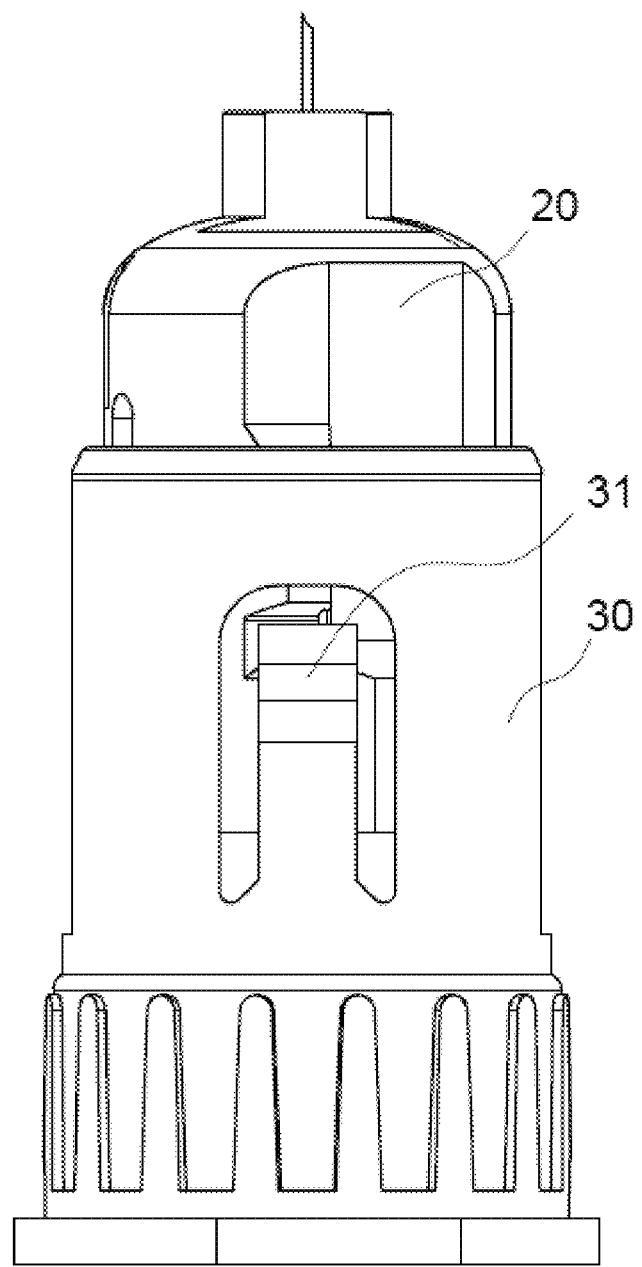
FIG. 1 is a structural view of a safe insulin pen needle according to this embodiment.
Figure 2:
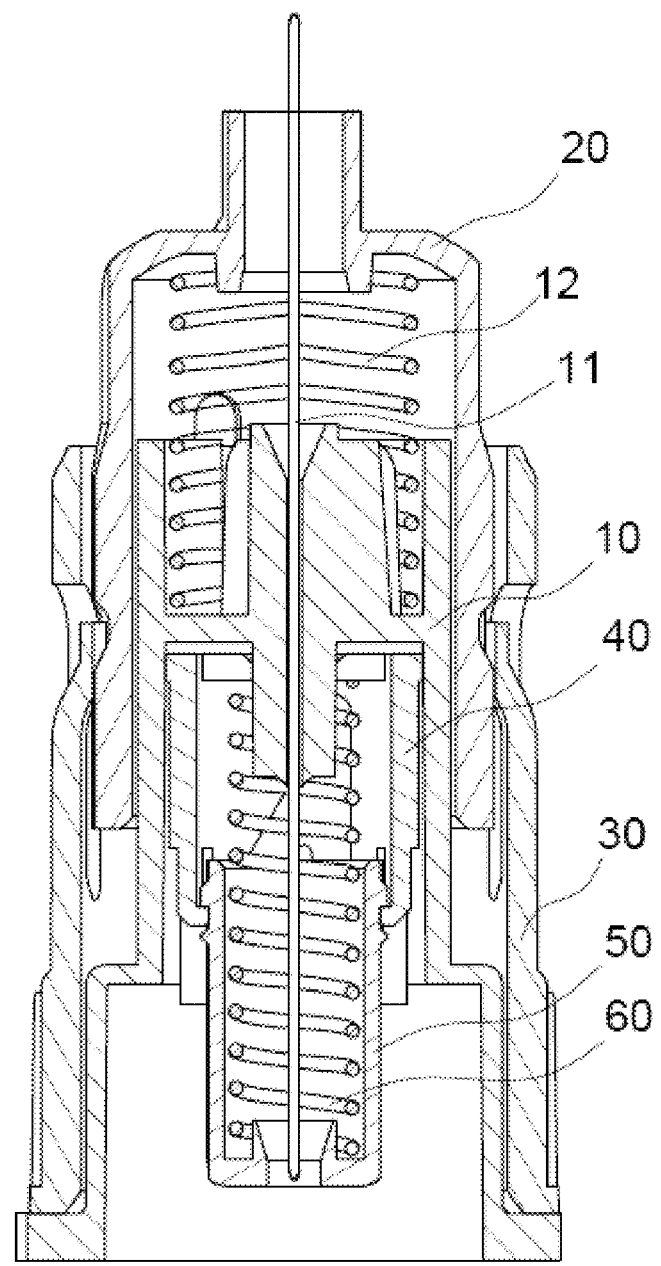
FIG. 2 is a cross-sectional structural view of the safe insulin pen needle shown in FIG. 1.

As shown in FIG. 1 and FIG. 2, a safe insulin pen needle of this embodiment includes at least a needle hub 10, a needle head protector 20 and a hub sheath 30. A needle tube 11 is mounted in the needle hub 10, and the needle tube includes at least a needle head 111 and a needle tail 112, and an infusion passage is formed between the needle head 111 and the needle tail 112.

Figure 3:
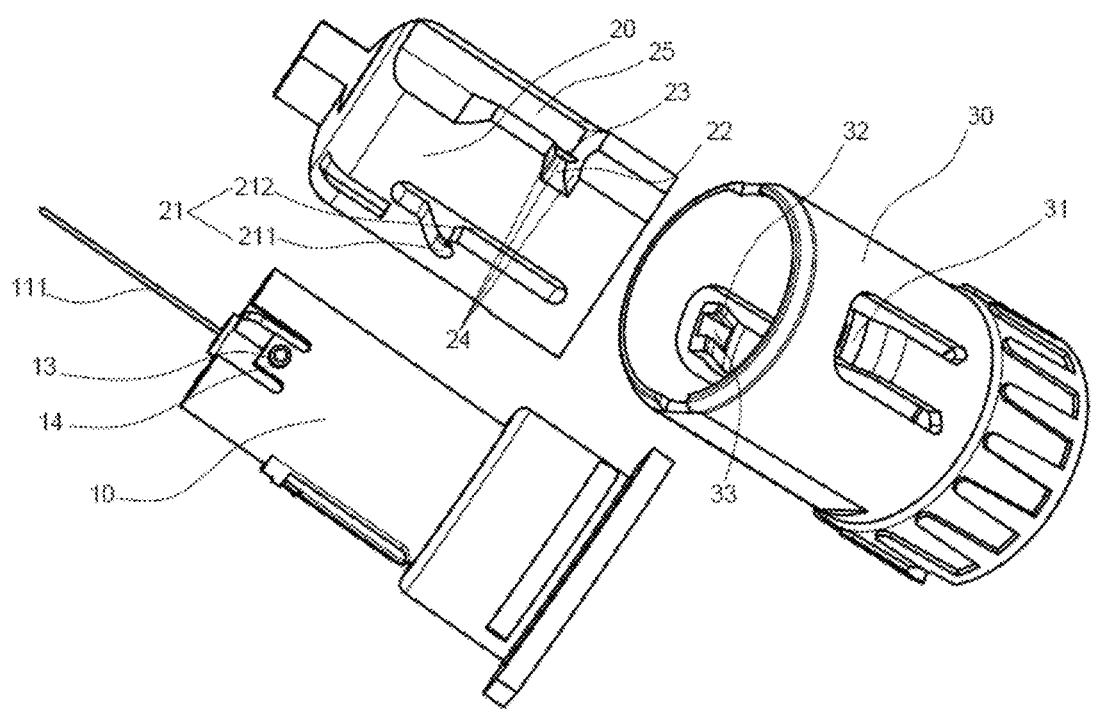
FIG. 3 is an exploded schematic view of the needle head protection structure of the safe insulin pen needle shown in FIG. 1.

As shown in FIG. 1-3, in this embodiment, the needle head protector 20 sleeves the needle head side of the needle hub 20, and a first axially compressed spring 12 is disposed between the needle hub and the needle head protector. Further, in this embodiment, a first clamping column 13 and a first guide groove 21 which are mutually matched are disposed between the needle hub and the needle head protector, and the first guide groove 21 includes a first initial fixing section 211 and a first axially extending trigger guide section 212.

Preferably, in this embodiment, the first clamping column is disposed on an outer wall of the needle hub, and the first guide groove is disposed on the needle head protector. Of course, as an alternative technical solution, the first clamping column can also be disposed on an inner wall of the needle head protector, and the first guide groove is disposed on the needle hub. In this embodiment, as a preferred implementation, the first clamping column is disposed on the cantilever structure 14. In this embodiment having such structure, disposing the first clamping column on the cantilever structure 14 facilitates the completion of the assembly between the needle head protector and the needle hub by using the deformation of the cantilever structure.

As a preferred implementation of this embodiment, there are two or three sets of first clamping columns and the first guide grooves which are mutually matched and are disposed uniformly in a circumferential direction. In this embodiment, when two or more sets of first clamping columns and the first guide grooves which are mutually matched are uniformly disposed in the circumferential direction, the axial movement of the needle head protector relative to the needle hub is more stable.

Further, in this embodiment, the hub sheath 30 sleeves the side of the needle hub away from the needle head, and the hub sheath is provided with at least one first elastic clamping jaw 31 in contact with the outer wall of the needle head protector. The function of the first elastic clamping jaw 31 is to prevent the needle head protector from moving backwards in the axial direction relative to the needle hub after the protection is in place. Preferably, the number of the first elastic clamping jaw 31 is two or three, and is preferably distributed uniformly in the circumferential direction.

The above-mentioned structures are all prior art, and the improvement points of this embodiment which are different from the prior art are described in detail below.

In the modified embodiment of this embodiment, as shown in FIG. 3, the outer wall of the needle protector is provided with a first initial fixing position 22 matched with the first elastic clamping jaw, and one side of the first initial fixing position 22 is provided with a first check flange 23 for preventing the first clamping column from entering the first initial fixing section 211 when the first clamping column 13 is located in the first trigger guide section 212.

In a preferred implementation, each side surface that encloses the first initial fixing position is a guide inclined surface 24, so that the first elastic clamping jaw is easily slid out from the first initial fixing position during the triggering process.

In a preferred implementation, a pair of oppositely disposed protruded jaws 32 is disposed on the side of the first elastic clamping jaw engaged with the first initial fixing position, and a partition section 33 adapted to the first check flange 23 is disposed between the pair of protruded jaws. In the structure of this embodiment, in an initial state, the pair of protruded jaws rides over the first check flange. Of course, as an alternative equivalent implementation, the number of the protruded jaw may be only one, and the protruded jaws may also be completely located in the first initial fixing position in the initial state.

For the safe insulin pen needle having the above structure, when the insulin is injected, the needle head protector is triggered, and the first clamping column enters the first trigger guide section from the first initial fixing section; during the process of pulling the needle after the insulin injection is completed, under the action of the elastic force of a first spring, the needle head protector moves axially relative to the needle hub. The guiding is achieved by the cooperation between the first clamping column and the first trigger guide section, the first elastic clamping jaw is always in contact with the first guide surface 25, since the first check flange is provided on one side of the initial fixing position, when a few users with the habit of rotating the insulin pen during pulling the needle rotate the insulin pen, the first check flange prevents the first elastic clamping jaw from entering the first initial fixing position again from the first guide surface. That is, the first clamping column can only move along the first trigger guide section and cannot enter the first initial fixing section again.

The safe insulin pen needle having the above structure effectively circumvents the risk of the automatic protection failure of the trigger protector on the needle head due to the rotation during pulling the needle after the injection of the insulin by some users through simple structure settings, so that the automatic protection of needle head protector on the needle head is safer and more reliable.

Embodiment 2

Figure 4:
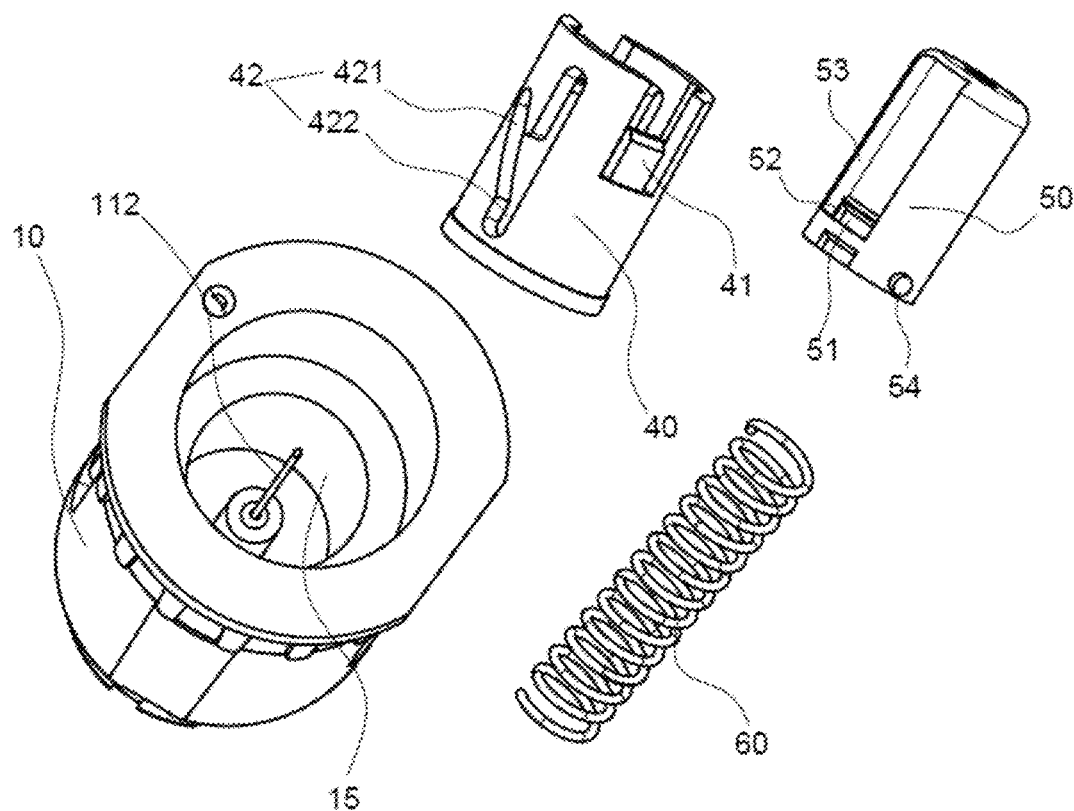
FIG. 4 is an exploded schematic view of the needle tail protection structure of the safe insulin pen needle shown in FIG. 1.

As shown in FIG. 2 and FIG. 4, according to the safe insulin pen of this embodiment, on the basis of Embodiment 1, a needle tail protection structure is disposed inside the needle tail end of the needle hub. In this embodiment, the needle tail protection structure includes a protective sleeve 40 and a needle tail protector 50 disposed in the needle tail protection chamber 15. A second axially compressed spring 60 is disposed between the protective sleeve 40 and the needle tail protector 50, and a second clamping column 54 and a second guide groove 42 which are mutually matched are disposed between the protective sleeve and the needle tail protector. The second guide groove 42 includes a second initial fixing section 421 and a second axially extending trigger guide section 422.

In a preferred implementation, as shown in FIG. 4, the second clamping column is disposed on an outer wall of the needle tail protector, and the second guide groove is disposed on the protective sleeve. Of course, as an alternative equivalent implementation, the second clamping column can also be disposed on the protective sleeve, and the second guide groove can be disposed on the needle tail protector.

In the structure of this embodiment, the needle tail protector is triggered during the screw-in connection of the insulin pen and the insulin pen needle, and a second spring is in a state of compression and energy storage, during the separation of the insulin pen from the insulin pen needle after the insulin injection is completed, the needle tail protector moves axially relative to the needle hub and completely covers the needle tail under the action of the spring force of the second spring and the guiding action of the second clamping column and the second trigger guide section. The technical problem that the needle tail portion may damage the user is effectively solved by disposing a needle tail protector with the same trigger mechanism as the needle head protector at the needle tail.

Embodiment 3

As shown in FIG. 2 and FIG. 4, according to the safe insulin pen of this embodiment, on the basis of Embodiment 2, the protective sleeve is further provided with a second elastic clamping jaw 41 in contact with an outer wall of the needle tail protector. The outer wall of the needle tail protector is provided with a second initial fixing position 51 matched with the second elastic clamping jaw, and one side of the second initial fixing position 51 is provided with a second check flange 52 for preventing the second clamping column from entering the second initial fixing section when the second clamping column is located in the second trigger guide section.

The safe insulin pen needle having the above structure has the following technical advantages:

During the screw-in connection of the insulin pen and the insulin pen needle, the needle tail protector is triggered, and the second spring is in a state of compression and energy storage, during the separation of the insulin pen from the insulin pen needle after the insulin injection is completed, the needle tail protector moves axially relative to the needle hub and completely covers the needle tail under the action of the spring force of the second spring and the guiding action of the second clamping column and the second trigger guide section. The technical problem that the needle tail portion may damage the user is effectively solved by disposing the needle tail protector at the needle tail.

In the process of rotating and separating the insulin pen from the insulin pen needle, due to the elastic force of the second spring, the free end face of the needle tail protector is always in contact with the end face of the insulin pen, when the insulin pen is rotated, it is highly probable that the needle tail protector is rotated at the same time under the action of the friction force, so that the risk of the needle tail protection failure is caused by the entrance of the second clamping column into the second initial fixing section again from the second trigger guide section. By disposing the second check flange on the side of the second initial fixing position matched with the second elastic clamping jaw, the second elastic clamping jaw can be effectively prevented from entering into the second initial fixing position from the second guide surface 53 due to rotation, i.e., the second clamping column is prevented from entering the second initial fixing section again from the second trigger guide section, thereby completely solving the technical problem of the above-mentioned needle tail protection failure, and the technical advantages of simple structure and reliable needle tail protection are achieved.

It should be noted that the needle tail protection structure in Embodiment 3 can be used in combination with the needle head protection structure in Embodiment 1, or can be used independently of the needle head protection structure in Embodiment 1.

Embodiment 4

Figure 5:
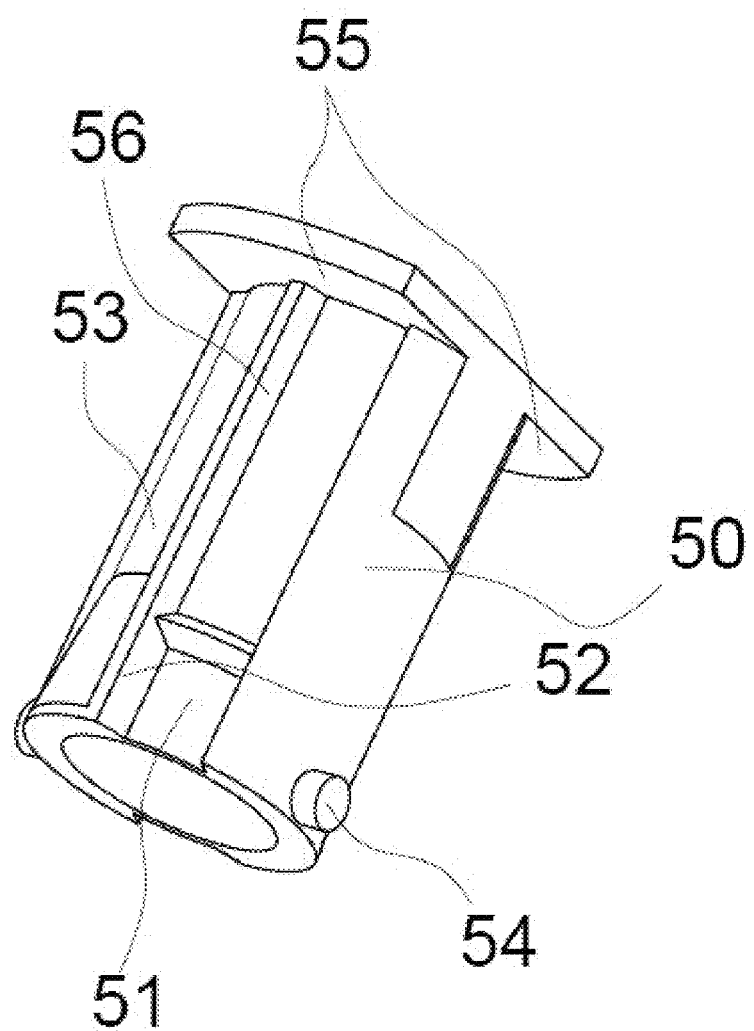
FIG. 5 is a structural view of a needle tail protector according to another embodiment.

The difference between this embodiment and Embodiment 3 is that the structure of the needle tail protector 50 is different. As shown in FIG. 5, according to the needle tail protector 50 of this embodiment, structurally, on the basis of the structure of the needle tail protector in Embodiment 3, a pair of radially extending flaps 55 is disposed at the free end of the needle tail protector 50. The purpose of such disposition is to prevent the free end of the needle tail protector 50 from entering the hole of the insulin pen connection end, causing the trigger failure during the connection of the insulin pen to the insulin pen needle of this embodiment.

In a preferred embodiment, an extension section 56 of the second check flange 52 extends all the way to the flap 55 to enhance the needle tail protection.

In summary, the above description is only the preferred embodiments of the present invention, and is not intended to limit the present invention. Any modifications, equivalent substitutions, improvements and the like made within the spirit and principles of the present invention should be included in protection scope of the present invention.

The invention claimed is:

1. A safe insulin pen needle, comprising at least:
   a needle hub, a needle tube being mounted in the needle hub and the needle tube comprising at least a needle head and a needle tail;
   a needle head protector, sleeving a needle head side of the needle hub, a first axially compressed spring being disposed between the needle hub and the needle head protector, a first clamping column and a first guide groove which are mutually matched being disposed between the needle hub and the needle head protector, and the first guide groove comprising at least a first initial fixing section and a first axially extending trigger guide section;
   a hub sheath, sleeving a side of the needle hub away from the needle head, and provided with at least one first elastic clamping jaw in contact with an outer wall of the needle head protector;
   wherein the outer wall of the needle head protector is provided with a first initial fixing position matched with the first elastic clamping jaw, and one side of the first initial fixing position being provided with a first check flange for preventing the first clamping column from entering the first initial fixing section when the first clamping column is located in the first trigger guide section.

2. The safe insulin pen needle according to claim 1, wherein the first clamping column is disposed on an outer wall of the needle hub, and the first guide groove is disposed on the needle head protector.

3. The safe insulin pen needle according to claim 1, comprising at least two sets of first clamping columns and first guide grooves which are mutually matched and disposed uniformly in a circumferential direction.

4. The safe insulin pen needle according to claim 1, wherein the first clamping column is disposed on a cantilever structure.

5. The safe insulin pen needle according to claim 1, wherein a pair of oppositely disposed protruded jaws is disposed on a side of the first elastic clamping jaw matched with the first initial fixing position, and a partition section adapted to the first check flange is disposed between the pair of protruded jaws.

6. The safe insulin pen needle according to claim 1, wherein the needle tail end of the needle hub is internally provided with a needle tail protection structure, the needle tail protection structure comprises a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove comprises at least a second initial fixing section and a second axially extending trigger guide section.

7. The safe insulin pen needle according to claim 2, wherein the needle tail end of the needle hub is internally provided with a needle tail protection structure, the needle tail protection structure comprises a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove comprises at least a second initial fixing section and a second axially extending trigger guide section.

8. The safe insulin pen needle according to claim 4, wherein the needle tail end of the needle hub is internally provided with a needle tail protection structure, the needle tail protection structure comprises a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove comprises at least a second initial fixing section and a second axially extending trigger guide section.

9. The safe insulin pen needle according to claim 5, wherein the needle tail end of the needle hub is internally provided with a needle tail protection structure, the needle tail protection structure comprises a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove comprises at least a second initial fixing section and a second axially extending trigger guide section-.

10. The safe insulin pen needle according to claim 6, comprising at least two sets of second clamping columns and second guide grooves which are mutually matched and disposed uniformly in a circumferential direction, the second clamping column is disposed on an outer wall of the needle tail protector, and the second guide groove is disposed on the protective sleeve.

11. The safe insulin pen needle according to claim 6, wherein a pair of flaps is disposed at a free end of the needle tail protector.

12. The safe insulin pen needle according to claim 10, wherein the protective sleeve is further provided with a second elastic clamping jaw in contact with the outer wall of the needle tail protector, the outer wall of the needle protector is provided with a second initial fixing position matched with the second elastic clamping jaw, and one side of the second initial fixing position is provided with a second check flange for preventing the second clamping column from entering the second initial fixing section when the second clamping column is located in the second trigger guide section.

13. The safe insulin pen needle according to claim 11, wherein the protective sleeve is further provided with a second elastic clamping jaw in contact with the outer wall of the needle tail protector, the outer wall of the needle protector is provided with a second initial fixing position matched with the second elastic clamping jaw, and one side of the second initial fixing position is provided with a second check flange for preventing the second clamping column from entering the second initial fixing section when the second clamping column is located in the second trigger guide section.

14. A safe insulin pen needle, comprising at least a needle hub, a needle tube being mounted in the needle hub and the needle tube comprising at least a needle head and a needle tail;
  wherein the needle tail end of the needle hub is internally provided with a needle tail protection structure, the needle tail protection structure comprises a protective sleeve and a needle tail protector, a second axially compressed spring is disposed between the protective sleeve and the needle tail protector, a second clamping column and a second guide groove which are mutually matched are disposed between the protective sleeve and the needle tail protector, the second guide groove comprises at least a second initial fixing section and a second axially extending trigger guide section; the protective sleeve is further provided with a second elastic clamping jaw in contact with an outer wall of the needle tail protector, the outer wall of the needle tail protector is provided with a second initial fixing position matched with the second elastic clamping jaw, and one side of the second initial fixing position is provided with a second check flange for preventing the second clamping column from entering the second initial fixing section when the second clamping column is located in the second trigger guide section.

15. The safe insulin pen needle according to claim 14, wherein a pair of flaps is disposed at a free end of the needle tail protector.

16. The safe insulin pen needle according to claim 14, wherein the second clamping column is disposed on the outer wall of the needle tail protector, and the second guide groove is disposed on the protective sleeve.

17. The safe insulin pen needle according to claim 14, comprising at least two sets of second clamping columns and second guide grooves which are mutually matched and disposed uniformly in a circumferential direction.

18. The safe insulin pen needle according to claim 15, wherein an extension section of the second check flange extends all the way to one of the pair of the flaps.

19. The safe insulin pen needle according to claim 15, wherein the second clamping column is disposed on the outer wall of the needle tail protector, and the second guide groove is disposed on the protective sleeve.

20. The safe insulin pen needle according to claim 18, wherein the second clamping column is disposed on the outer wall of the needle tail protector, and the second guide groove is disposed on the protective sleeve.

* * * * *